US012642449B2

(12) United States Patent
Fregosi et al.

(10) Patent No.: US 12,642,449 B2
(45) Date of Patent: Jun. 2, 2026

(54) DEVICE AND ASSOCIATED METHODS FOR SIMULTANEOUS MEASUREMENT OF PULMONARY VENTILATION AND METABOLIC RATE

(71) Applicant: Arizona Board of Regents on Behalf of the University of Arizona, Tucson, AZ (US)

(72) Inventors: Ralph Fregosi, Tucson, AZ (US); Christina Hoyer-Kimura, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 378 days.

(21) Appl. No.: 18/316,075

(22) Filed: May 11, 2023

(65) Prior Publication Data

US 2023/0363664 A1 Nov. 16, 2023

Related U.S. Application Data

(60) Provisional application No. 63/340,600, filed on May 11, 2022.

(51) Int. Cl.
| | |
|---|---|
| *A61B 5/08* | (2006.01) |
| *A61B 5/00* | (2006.01) |
| *A61B 5/083* | (2006.01) |
| *A61B 5/097* | (2006.01) |
| *A61B 5/318* | (2021.01) |

(52) U.S. Cl.
CPC .......... *A61B 5/0803* (2013.01); *A61B 5/0833* (2013.01); *A61B 5/0836* (2013.01); *A61B 5/097* (2013.01); *A61B 5/318* (2021.01); *A61B 5/6805* (2013.01); *A61B 2503/40* (2013.01)

(58) Field of Classification Search
CPC ..... A61B 5/0803; A61B 5/318; A61B 5/0833; A61B 5/0836; A61B 5/097; A61B 5/6805; A61B 2503/40
See application file for complete search history.

(56) References Cited

U.S. PATENT DOCUMENTS

| | | | | |
|---|---|---|---|---|
| 4,582,055 A * | 4/1986 | McDougal | ............... | A61D 7/04 |
| | | | | 128/203.29 |
| 8,628,479 B2 * | 1/2014 | Lomask | ............... | A61B 5/0806 |
| | | | | 600/529 |
| 2006/0258914 A1 * | 11/2006 | Derchak | .............. | A61B 5/6805 |
| | | | | 600/595 |
| 2006/0278218 A1 * | 12/2006 | Hoffman | .............. | A61B 5/0806 |
| | | | | 128/200.24 |
| 2009/0223460 A1 * | 9/2009 | Starr | ...................... | A01K 1/031 |
| | | | | 119/420 |

* cited by examiner

*Primary Examiner* — Eric F Winakur

(74) *Attorney, Agent, or Firm* — Polsinelli PC

(57) ABSTRACT

Various examples of a device for simultaneous measurement of pulmonary ventilation and metabolic rate are disclosed including a dual chamber configuration providing values for pulmonary ventilation and metabolic rate that compare favorably with the gold standard approaches.

20 Claims, 6 Drawing Sheets

100

100

100

170

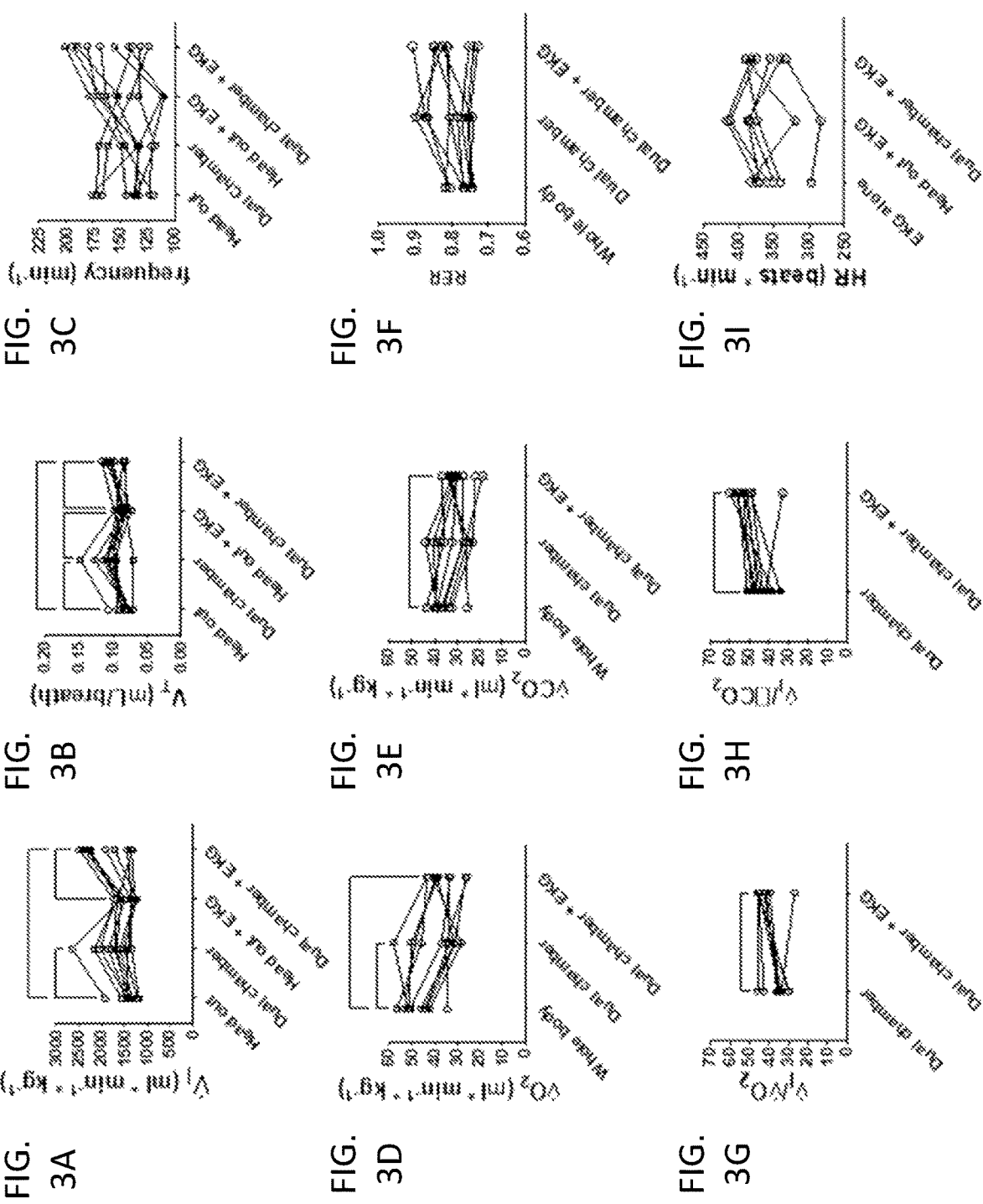

DEVICE AND ASSOCIATED METHODS FOR SIMULTANEOUS MEASUREMENT OF PULMONARY VENTILATION AND METABOLIC RATE

CROSS REFERENCE TO RELATED APPLICATIONS

This is a non-provisional application that claims benefit to U.S. Provisional Application Ser. No. 63/340,600, filed on May 11, 2022, which is herein incorporated by reference in its entirety.

GOVERNMENT SUPPORT

This invention was made with government support under Grant No. HD071302 awarded by the National Institutes of Health. The government has certain rights in the invention.

FIELD

The present disclosure generally relates to technologies associated with plethysmography, and in particular, to simultaneous measurement of pulmonary ventilation and metabolic rate (e.g., in neonatal rodents).

BACKGROUND

In recent decades, a host of cellular, molecular, and genetic approaches have been developed to interrogate the inner workings of the motor and sensory components that underlie the control of breathing. It is often critical to buttress these approaches with a behavioral assay, which has led to the widespread use of plethysmography to measure pulmonary ventilation in awake neonatal rodents. Best practice requires correcting changes in ventilation to the corresponding change in metabolic rate, which is the main driver of pulmonary ventilation. This is especially important when studying the response to hypoxia, as metabolic rate drops precipitously in the hypoxic neonate.

The approaches most often used are whole-body and head-out plethysmography. The advantages and disadvantages of each have been widely discussed but can be summarized as follows: In whole body plethysmography, the animal is studied in an enclosed chamber, which allows the animal to be studied awake and unrestrained, and simultaneous measurement of metabolic rate is straightforward. With this method, pressure changes within the chamber are due to both the compression and expansion of alveolar gas as well as changes in volume due to the difference in temperature and humidity between gas in the lungs and gas in the chamber, with the latter contributing proportionally more to the total pressure change. This can be problematic in small animals because the pressure changes due to heating and humidification of inhaled gas are very small, making precise measurements of temperature and humidity critical. As a result, some investigators resort to measuring frequency of breathing only, which results in an incomplete behavioral assessment. To circumvent these issues, head out plethysmography was developed. Here, the animal breathes from the atmosphere, and the remainder of the body is enclosed in a chamber. The gas inhaled from the environment expands the pup's thorax resulting in a change in pressure that is directly proportional to the change in lung volume. While this method makes it easier to measure lung volume changes, the disadvantages include the neck seal used to isolate the head from the chamber which restrains movement as well as the difficulty with measuring metabolic rate.

It is with these observations in mind, among others, that various aspects of the present disclosure were conceived and developed.

SUMMARY

The following presents a simplified summary of various aspects described herein. This summary is not an extensive overview and is not intended to identify key or critical elements or to delineate the scope of the claims. The following summary merely presents some concepts in a simplified form as an introductory prelude to the more detailed description provided below. Corresponding apparatus, methods/processes, systems, and computer-readable media are also within the scope of the disclosure.

Various in vitro neonatal rodent models have been developed to study the control of breathing, but translation of the information requires a behavioral assay, which has led to the widespread use of plethysmography to measure breathing in awake neonatal rodents. Best practice requires correcting changes in ventilation to the corresponding change in metabolic rate, which is the main driver of pulmonary ventilation. The presumptive gold standards for measuring pulmonary ventilation and metabolic rate are head out and whole-body plethysmography, respectively. Obtaining measures of both simultaneously is ideal, though technically difficult. Here a simple, inexpensive home-made dual chamber approach for simultaneous measurement of pulmonary ventilation and metabolic rate is described. It was found that the dual chamber provides values for pulmonary ventilation and metabolic rate that compare favorably with the gold standard approaches. It also proved useful for comparing the hypoxic ventilatory response in controls and nicotine exposed neonatal rat pups, which was blunted in the latter.

In general, aspects of the present inventive concept further relate to:

An inexpensive and efficient method to construct device including a dual chamber plethysmograph configuration which can be sized for neonatal rodents.

The device proved to accurately measure pulmonary ventilation and metabolic rates simultaneously.

This device will provide an inexpensive alternative approach for investigators that need to assay the ventilatory and whole-body metabolic phenotype of neonatal rodents.

Aspects of the present disclosure can take the form of a system, device, and one or more methods thereof as indicated herein.

BRIEF DESCRIPTION OF THE DRAWINGS

FIGS. 3A-3I are illustrations of additional representative recording and comparison data as described herein.

Corresponding reference characters indicate corresponding elements among the view of the drawings. The headings used in the figures do not limit the scope of the claims.

DETAILED DESCRIPTION

Various examples herein relate to an inventive concept that accommodates the simultaneous use of head-out and whole-body plethysmography. A "dual chamber" configuration or design is implemented where an animal can be placed in a head out chamber, and the entire head out chamber is then inserted or otherwise positioned into a larger chamber that is sealed from the environment except for a steady bias flow of gas. Example construction of the chamber is described, and validation data is presented. Using a repeat-measures, randomized experimental design, it was found that the dual chamber configuration provides values for pulmonary ventilation and metabolic rate that compare favorably with values obtained using more traditional approaches.

General Materials and Methods

Dual Chamber Design and Dimensions, and EKG Vest.

Figure 1A:
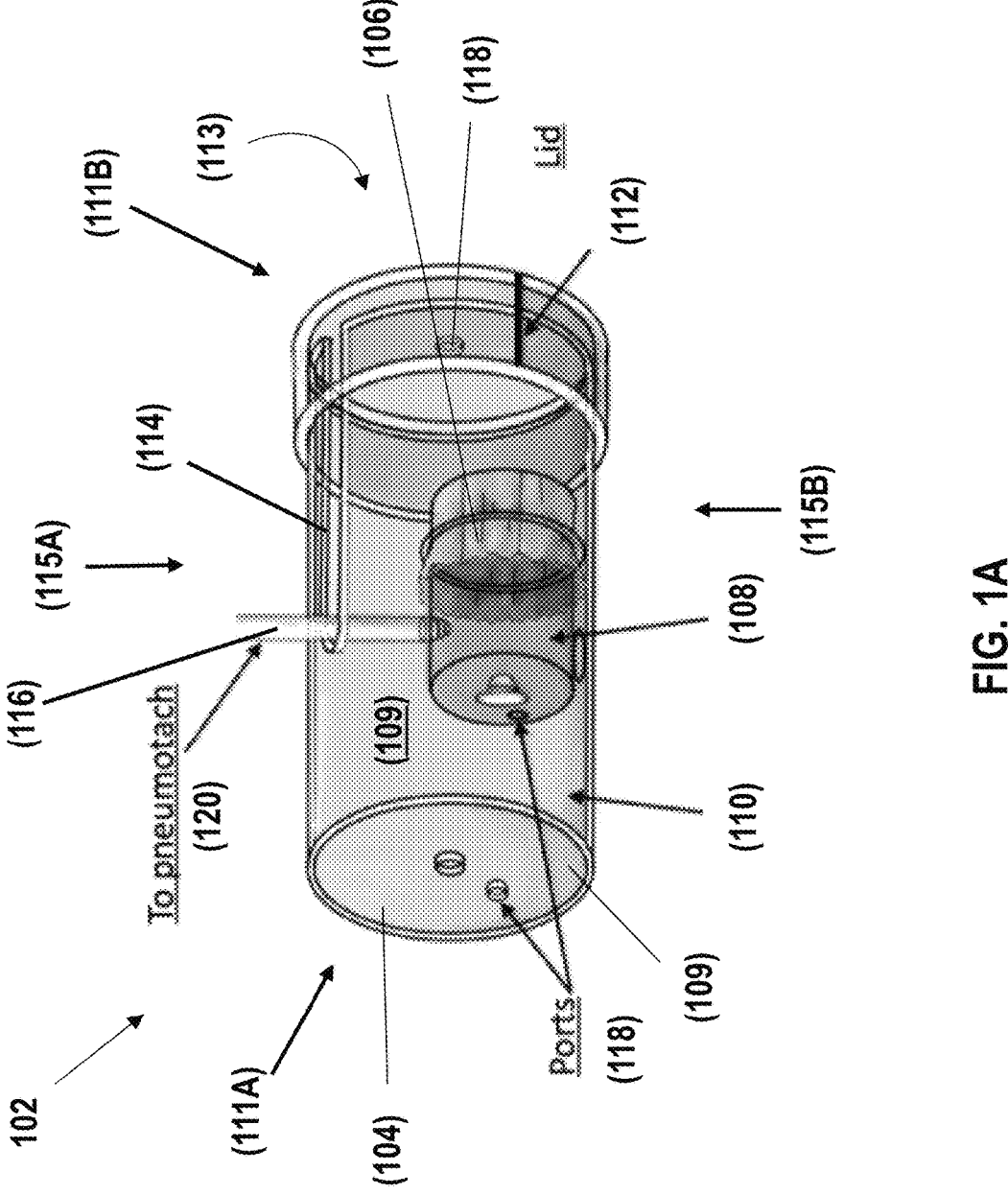
FIG. 1A is a perspective view of a device including a dual chamber configuration for measuring breathing frequency and airflow as described herein.

Referring to FIG. 1A, a device 102 of a system 100 including a "chamber-in-chamber" or "dual-chamber" configuration is shown that accommodates simultaneous measurement of pulmonary ventilation and metabolic rate as described herein. The device 102 may include a body 104 and may be generally comprised of a head-out plethysmograph 106 defined by a (head-out) first chamber 108, with the plethysmograph 106 positioned along a channel 109 defined by a second (outer) chamber 110, such that the second chamber 110 at least partially encloses the first chamber 108. As indicated, the channel 109 extends between a closed end 111A of the second chamber and an open end 111B, and the device 102 can include a lid 112 that can be positioned along the open end 111B of the second chamber 110 to seal an opening 113 in communication with the channel 107 along the open end 111B, thereby enclosing the first chamber 108 within the second chamber 110. As further shown, the device 102 can include an access slot 114 defined along a first side 115A of the device opposite a second side 115B. Gum rubber or other such suitable component can be used to seal the access slot 114 as needed and further described herein. In general, air can be pulled through the second chamber 110 by an $O_2$ and $CO_2$ analyzer for open circuit measurement of metabolic rate.

One example of the inner, head-out first chamber 108 was made from a 60-cc plastic syringe cut to a length of 70 mm. A Luer lock end was implemented and used for calibration via injection of known volumes of air. A 3 mm-diameter hole was drilled into the top and a plastic Luer Lock fitting was epoxied in place and connected to a ¼ inch diameter thick, 4 cm long thick-walled (1 mm) Tygon tube, which is connected to the inflow tube (116) of a Hans-Rudolph pneumotachometer, indicated as pneumotach 120 in FIG. 1A. (e.g., Model 8430, 3 L/min max flow). One or more additional holes, with diameter about 2 mm can be drilled and used as conduits for EKG wires and thermocouple. The location of these holes is based on preference. After the wires or thermocouple are passed through, utility wax (Coltene Whaledent utility wax round strips, item #900-H00817, Florida Dental Supply) can be applied as a sealant.

In some examples, the second (outer) chamber 110 can be made from thick-walled (6 mm) Plexiglass with an outer diameter of 50 mm and an inner diameter of 38 mm. The lid 112 and the closed end 111A of the second chamber 110 may each include two ports (ports 118), with one 5 and one 3 mm diameter. The 5 mm holes are threaded to accommodate a 2 mm id nylon hose barb (Masterflex Fittings, item #EW-41517-04) for connecting gas inflow and outflow tubing. The 3 mm holes accommodate passage of the thermocouple and EKG lead wires. The access slot 114 may be formed by a cut into the open end (111B) of the second chamber 110 that is 50 mm long and about 12 mm wide. This allows the inner, head-out first chamber 108 to be inserted easily and accommodates Tygon tubing that is connected to the pneumotach (120). After the head-out chamber 108 is inserted, vacuum grease is applied to the inner surface of the lid 112, and the access slot 114 may be covered with a piece of gum rubber (Gum Rubber Sheet Gasket, 1/16" Thick, from e.g., Amazon.com®). The gum rubber has a hole sized to accommodate the inflow tube 116 and/or tubing that connects to the pneumotachometer 120 and is 10 mm longer and 20 mm wider than the exposed portion of the access slot 114. The $CO_2$ analyzer (FIG. 1C) may then be used to check for leaks, and when found they may be sealed with vacuum grease.

Exemplary non-limiting dimensions of the device 102 are as follows. The first chamber 108 can be 70 mm long, can include a 2 mm inner diameter (ID), and a 30 mm outer diameter (OD). The second chamber 110 can be 105 mm long, can include a 38 mm ID, and a 50 mm OD. The access slot 114 can be 50 mm long and 12 mm wide. The lid 112 can be 30 mm long and can have a 50 mm ID and a 63 mm OD. The foregoing dimensions can vary depending upon the intended animal to be analyzed; e.g., increased or decreased proportionally as desired for different sized subjects. In other words, the dimensions of both the first chamber 108 and the second chamber 110 can be adjusted for larger (or smaller) animals, though the head-out method is difficult in animals older than P12 as they do not tolerate restraint and often break the neck seal.

For traditional whole-body plethysmography, examples of the device 102 include a smaller version of the second chamber 110 shown in FIG. 1A. This chamber was also made of Plexiglass, with an OD of 32 mm, an ID of 28 mm and a wall thickness of 2 mm. In this example, the lid is 27 mm long, with a 50 mm OD, 35 mm ID, and wall thickness of 7.5 mm. As with the larger second chamber 110, the lid 112 and closed end 111A have gas inflow and outflow ports fitted with 2 mm ID nylon hose barbs, with another 3 mm diameter hole for the thermocouple probe. As with the larger second chamber 110, the inner surface of the lid 112 can be coated with vacuum grease before attachment, and leaks around the thermocouple port can be sealed with wax.

Figure 1B:
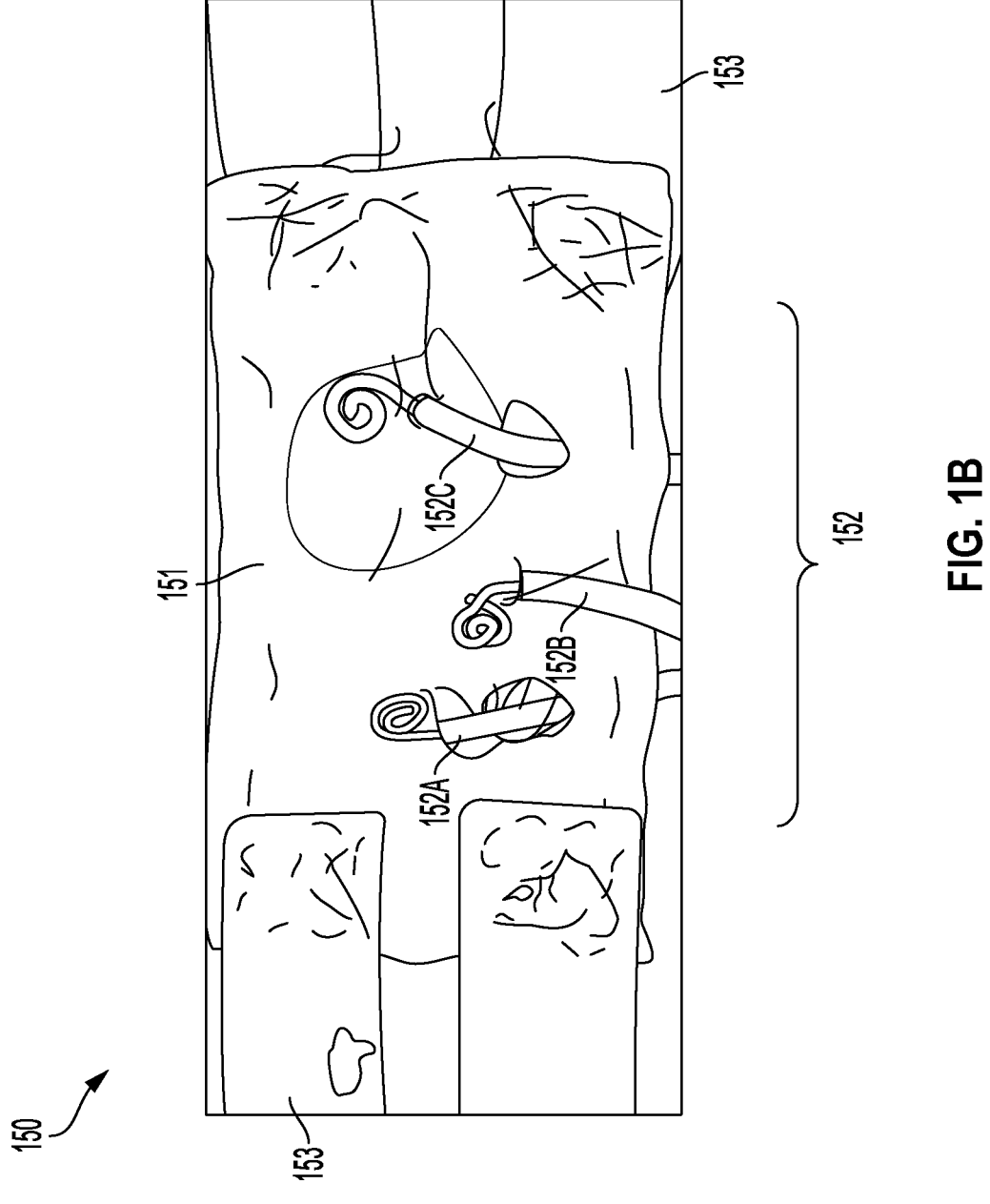
FIG. 1B is a photograph of a portion of a vest with electrodes for measuring heart rate associated with the device of FIG. 1A.

Referring to FIG. 1B, to accompany the device 102, the system 100 can further include a vest 150 that includes one or more electrodes referenced herein; e.g., three electrodes 152 (including by example electrode 152A, electrode 152B, and electrode 152C) for the measurement of the EKG to obtain heart rate. Examples of the vest 150 can be made from a vest base 151 which can include a piece of canvas sized for 1-2-week-old rat pups, with dimensions 50×25 mm. Four strips (153) which can include Velcro or the like, two with loops on one side and two with hooks on the other, can be sewn to the vest base 151 to secure the vest 150 to the animal. The electrodes 152 can be implemented by coiling a 2 cm length of coated stainless-steel wire (0.2 mm, A-M Systems, Inc.), smashing it flat with a hammer, and filing it smooth. The electrodes 152 can then be soldered to lead wire for connection to an amplifier (see below) and secured to the vest base 151 with thread or other such fastening component (e.g., staples, adhesive, etc.).

Figure 1C:
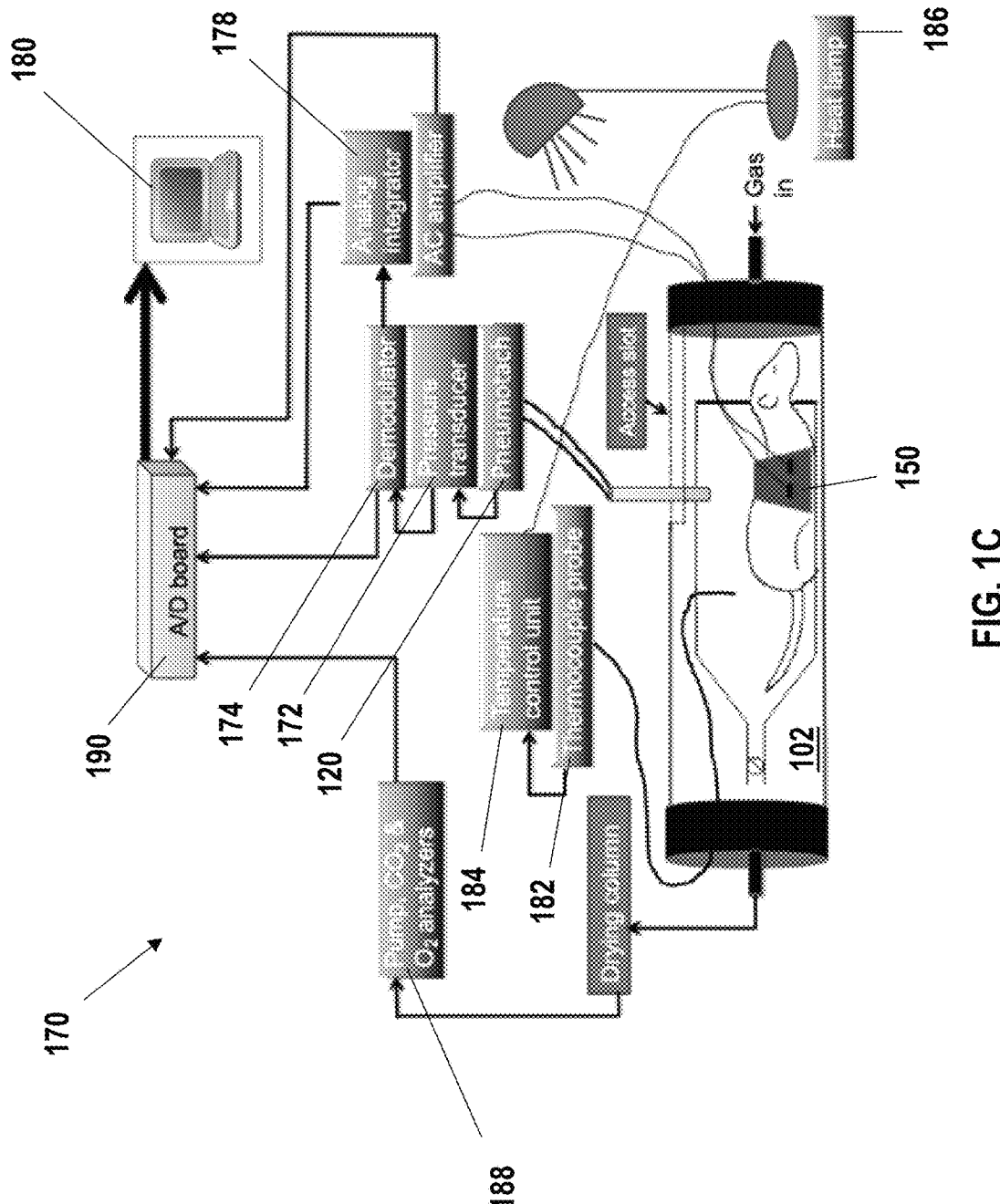
FIG. 1C is a schematic diagram of the device of FIG. 1A interfaced with exemplary equipment for recording pulmonary ventilation, metabolic rate, and heart rate.

Referring to FIG. 1C, exemplary recording equipment 170 associated with the device 102 and system 100 is shown for recording, e.g., pulmonary ventilation, metabolic rate, and heart rate. In some examples, the two ports (not shown) of the pneumotachometer 120 were attached to the positive and negative ports of a pressure transducer 172 with a range of ±2 cm $H_2O$ (Validyne DP45-16, Northridge, CA), and amplified with a Validyne Carrier demodulator 174. The pressure signal, which is proportional to the airflow rate, was sent in parallel to an analog integrator 178 (Grass model 7, Quincy, MA) and an A/D board 190. The inspiratory phase of the airflow signal was integrated to derive the inspired tidal volume ($V_T$). The digitized airflow signal and inspired $V_T$ signal were displayed on a computer screen 180 (see FIG. 2) and stored using Spike II software (Cambridge Electronic Design). The head-out plethysmograph 106 was calibrated by injecting 0.05, 0.1 and 0.15 ml into the chamber 108 to establish a relation between known volume and the amplitude of the $V_T$ signal. The thermocouple probe 182 was attached to a control unit 184 (TCAT-1A Temperature Controller, Physitemp, Clifton, NJ) that maintained chamber temperature at 33±0.15° C. (mean±SD) by controlling a heat lamp 186. This ambient temperature corresponds to normal nesting conditions for neonatal rats.

In an example test, metabolic rate was measured with the dual chamber device 102 and with standard whole-body plethysmography. The gas analyzer(s) 188 pulled air through the plethysmographs at a rate of 100 ml/min for the standard whole-body plethysmograph, and 150 ml/min for the larger dual chamber (defined by device 102). The effluent gas exiting the device 102 passed through a Dri-Rite canister and then to $O_2$ and $CO_2$ analyzers (iWorx GA 200). The output from the $CO_2$ and $O_2$ sensors was digitized using the Spike II A/D board 190 and software as above (FIG. 1C). Temperature was monitored and maintained as described herein.

Validation of the Dual Chamber for In Vivo Plethysmography.

To validate the new dual chamber approach (of device 102) for measuring pulmonary ventilation, a study was conducted of 10 animals (5 male, 5 female) aged P2-P5 in both the standard head out plethysmography chamber and the dual chamber. To evaluate the accuracy of metabolic rate measurements in the dual chamber, it was decided to also measure metabolic rate in a traditional whole-body plethysmograph sized for small animals. Thus, each animal was studied in each of four conditions, with the order of presentation randomized: head-out chamber alone; dual chamber; head-out chamber plus an EKG vest (see below); dual chamber plus the EKG vest. Measurements were made for 30 min in each condition to achieve a steady state, and the animals were given a 30 min recovery between measurements. Key comparisons include inspired $V_T$, breath frequency, their product (pulmonary ventilation rate, $\dot{v}_I$), oxygen consumption ($\dot{v}O_2$) $CO_2$ production ($\dot{v}CO_2$), the respiratory exchange ratio (RER, $\dot{v}CO_2/\dot{v}O_2$), and heart rate.

To validate the dual chamber model under experimental conditions, the rates of ventilation and metabolism were measured in 22 control rat pups (14 male, 8 female) and 22 pups (12 male, 10 female) that were exposed to nicotine during development (developmental nicotine exposure, DNE). The experiment was designed to compare the ventilatory response to a 30 sec exposure to $N_2$, which was done by bleeding gas into the chamber at roughly the same rate at which the gas was removed by the $O_2/CO_2$ analyzer pump. To regulate the compressed gas flow rate, a calibrated Rotameter (Matheson) was used. Measurements of the ventilatory and metabolic responses evoked by compressed humified air (control) and compressed humidified $N_2$ (stimulus) were made. Pups were exposed to nicotine via an osmotic minipump that was implanted into the timed-pregnant mother on gestational day four as described previously. The pump was loaded to deliver nicotine bitartrate at a dose of 6 mg/kg/day for 28 days. Pups were studied within the first six days of life, so exposure was via the placenta in utero and through breast milk after birth. In control animals the osmotic pump was loaded with saline.

Statistics.

To compare the different methods for measuring ventilation and metabolism referenced herein, it was decided to apply one-way, repeated measures analysis of variance (ANOVA). If the ANOVA was significant, paired contrasts were analyzed with the Bonferroni post hoc procedure. To mitigate effects of differences in body weight, and for ease of comparison with published values, $\dot{v}_I$, $\dot{v}O_2$ and $\dot{v}CO_2$ are expressed as ml*$min^{-1}$*kg body weight-. The performance of the dual chamber for detecting differences in the ventilatory and metabolic responses to a brief $N_2$ challenge resulting from nicotine exposure was also studied. These experiments were analyzed with a two-way mixed model repeated measures ANOVA, with treatment group (control, DNE) and gas condition (compressed air or compressed $N_2$) the main factors. As above, it was decided to use the Bonferroni post hoc procedure when the ANOVA was significant. All values in the text are expressed as the mean±1 SD. For all tests, statistical significance was defined as a P-value of ≤0.05. Prism software (GraphPad Software, San Diego, CA) was used for all statistical analyses.

RESULTS

Figure 2:
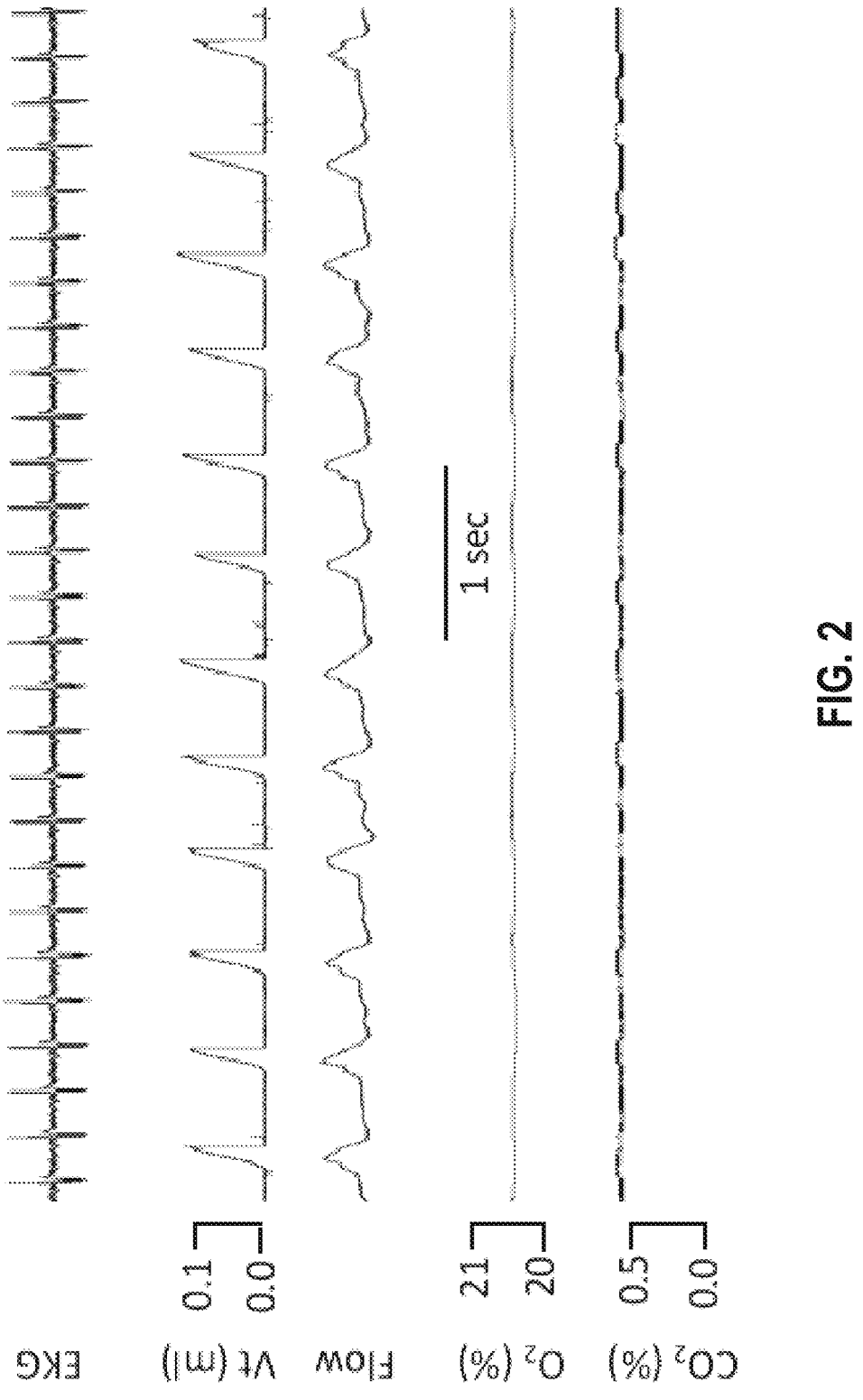
FIG. 2 is an image illustrating representative recording and comparison data including the EKG, the time integral of inspired airflow, the peak height of which is equivalent to inspired tidal volume; airflow signal from the pneumotach (inspiration upwards), and the $CO_2$ and $O_2$ concentrations (in percent) in the chamber effluent gas.

The age distribution for the 10 pups studied to compare the dual chamber with some selected existing approaches was: P2, N=2; P3, N=3, P4, N=3 and P5, N=2. Body weight ranged from 8.5-12.9 g and averaged 10.9±1.2 g. A representative recording from an animal studied in the device 102 including the dual chamber configuration and wearing the EKG vest 150 is shown in FIG. 2. The traces, from top down, include the EKG, inspired $V_T$, airflow, and the concentrations of $O_2$ and $CO_2$ in the chamber effluent. Note the stability of breathing and heart rate during this epoch, as well as the quality of the airflow tracing.

FIGS. 3A-3I show all data used to assess the concordance between the dual chamber (of device 102) and more traditional approaches for measuring pulmonary ventilation and metabolic rate. $\dot{v}_I$ averaged 1445±207 ml*$min^{-1}$*$kg^{-1}$ in the head out chamber and was roughly 20% higher in the dual chamber (1801±207 ml*$min^{-1}$*$kg^{-1}$) (P<0.01, FIG. 3A). Variability in the dual chamber was also higher than that obtained with the standard head-out approach (coefficient of variation (CV) 14 and 11.5%, respectively). The higher $\dot{v}_I$ in the dual chamber compared to the head-out plethysmograph was due to higher $V_T$ (FIG. 3B), as frequency did not differ between any of the trials (FIG. 3C). $V_T$ averaged 0.084±0.01 ml/breath in the head-out chamber and 0.11±0.02 ml/breath in the dual chamber (P<0.01, FIG. 3B). Attaching the EKG vest during either head-out or dual-chamber plethysmography had no significant influence on $V_T$ or $\dot{v}_I$ (FIG. 3A).

$\dot{v}O_2$ (FIG. 3D) averaged $47\pm6.5$ ml*min$^{-1}$*kg$^{-1}$ in the whole-body chamber, $40\pm10$ in the dual chamber (P<0.05, whole body vs. dual chamber), and $36\pm6.4$ ml*min$^{-1}$*kg$^{-1}$ when the dual chamber was combined with the EKG vest (P<0.01, whole body vs. dual chamber+vest). $\dot{v}CO_2$ measured in the whole-body chamber (FIG. 3E) averaged $37\pm5$ ml*min$^{-1}$*kg$^{-1}$, which was not different than that measured in the dual chamber ($32\pm7$ ml*min$^{-1}$*kg$^{-1}$. $\dot{v}CO_2$ measured in the dual chamber while pups wore the EKG vest averaged $30\pm5.5$ ml*min$^{-1}$*kg$^{-1}$ (P<0.001 compared to the whole-body chamber, FIG. 3E). RER averaged $0.77\pm0.03$ in the whole-body plethysmograph, $0.81\pm0.06$ in the dual chamber and $0.81\pm0.06$ when the dual chamber was combined with the EKG vest (P=NS, FIG. 3F). The gas convection requirement for $O_2$ ($\dot{v}_I/\dot{v}O_2$) averaged, respectively, $36\pm5$ and $42\pm6$ in the dual chamber and in the dual chamber with the pup wearing the EKG vest (FIG. 3G, P<0.05). The $\dot{v}_I/\dot{v}CO_2$ ratio averaged $44\pm5$ and $52\pm7$ in the dual chamber and the dual chamber plus vest (FIG. 3H, P<0.05).

Further, heart rate was analyzed in each pup under each of three conditions; resting quietly on a paper towel; in the head-out plethysmograph; and in the dual chamber plethysmograph. Heart rate averaged $354\pm29$ on the paper towel, $368\pm49$ with the pup in the head-out plethysmograph, and $366\pm24$ b/min with the pup in the dual chamber (P=NS, FIG. 3I).

Figure 4A:
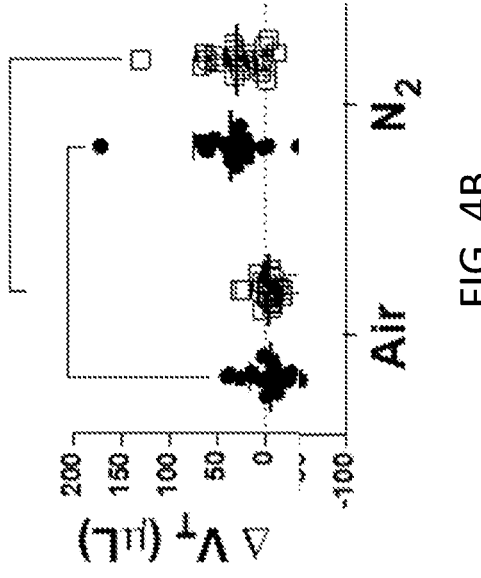
FIGS. 4A-4D are images illustrating a summary of the ventilatory responses to a brief N2 challenge recorded with the device described herein.
Figure 4B:
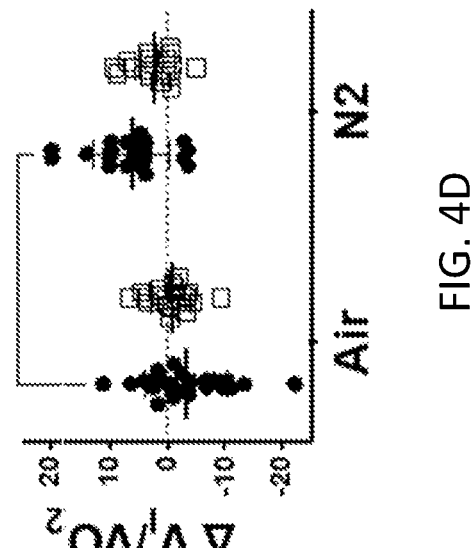
Figure 4C:
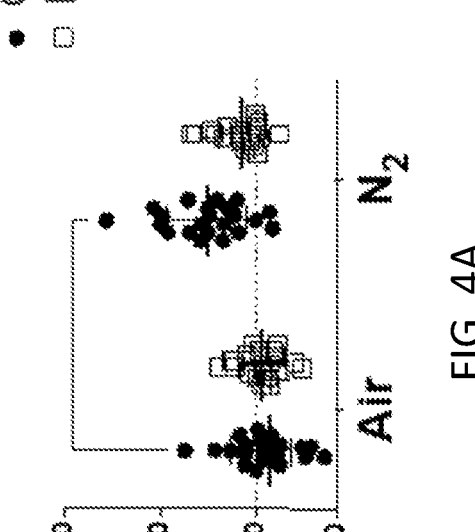
Figure 4D:
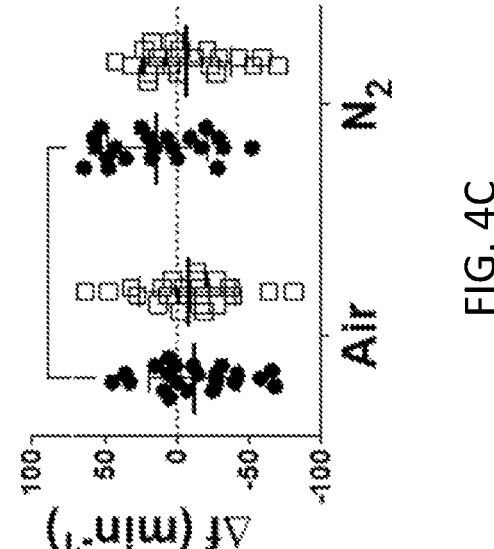

Referring to FIGS. 4A-4D, the $N_2$ challenge studies were done to evaluate the dual chamber approach under experimental conditions. 22 saline-exposed and 22 DNE pups of either sex were studied, aged P1-P6. Body weight averaged $11\pm2$ g in controls and $9.6\pm2.6$ g in DNE (P=0.17). As shown in FIG. 4A, the addition of compressed air did not significantly alter $\dot{v}_I$, $\dot{v}_T$, frequency or $\dot{v}_I/\dot{v}O_2$ in either treatment group. Bleeding $N_2$ into the chamber increased $\dot{v}_I$ and $\dot{v}_T$ significantly in both groups (FIG. 4A & FIG. 4B), but frequency increased only in the control group (FIG. 4C). As a result, the change in $\dot{v}_I$ was greater in control compared to DNE pups (FIG. 4A), as confirmed with an unpaired t-test (t=3.48, P=0.0012). Exposure to compressed $N_2$ increased $\dot{v}I/\dot{v}O_2$ in control pups, but not in the DNE pups (FIG. 4D). Animals.

All data was obtained from experiments approved by the Institutional Animal Care and Use Committee at The University of Arizona and comply with the ARRIVE guidelines and the National Institutes of Health guide for the care and use of Laboratory animals. A total of 31 male and 23 female animals aged P2-P6 were used, though no sex differences were detected in any of the protocols, so the data are pooled.

DISCUSSION

Measurements of pulmonary ventilation, metabolic rate, and heart rate obtained with a homemade dual chamber plethysmograph were compared to those measured using the more traditional head-out and unrestrained whole-body plethysmographs, broadly considered as the gold standards for measuring ventilation and metabolism, respectively, in neonatal rodents. In view of these measurements, the dual chamber approach accommodated by the device 102 described herein is believed to be novel and inventive. The validation studies involved recording breathing frequency and $V_T$ using both the standard head-out and the dual chamber method in each of 10 pups, ranging in age from P2-P5. Validation of metabolic rate compared values in the dual chamber with those obtained in a whole-body plethysmograph. There was no difference in breathing frequency measured in the head-out versus dual chamber configuration, though $V_T$ and $\dot{v}_I$ were significantly higher in the dual chamber. On average, $\dot{v}_I$ was 20% higher in the dual chamber than in the head-out chamber ($1801\pm393$ vs $1445\pm207$ ml*kg*min$^{-1}$), and the data were more variable (coefficient of variation 22 vs. 14%). However, the difference was consistent, with 9 of the 10 pups having a higher value in the dual chamber than in the head-out chamber. Similarly, both $\dot{v}O_2$ and $\dot{v}CO_2$ were lower in the dual chamber than in the whole-body plethysmograph in 8 of 10 pups. The RER was similar in both plethysmographs, indicating that the difference in $\dot{v}O_2$ and $\dot{v}CO_2$ between the chambers were of similar magnitude.

The dual chamber can be used to assess differences between treatment groups, or between interventions within a treatment group. It was not understood the reason for the lower $\dot{v}O_2$ in the dual chamber compared to that measured in a traditional, sealed plethysmograph. It could simply be the result of the larger volume required in the dual chamber, which reduces the precision of measures of effluent $O_2$ and $CO_2$ concentrations.

The dual chamber approach evaluated here proved useful for studying the influence of perinatal nicotine exposure on hypoxic sensitivity. This experiment was used because there is data showing that nicotine exposure does reduce some aspects of the hypoxic ventilatory response in one-week-old neonatal rat pups (Fuller et al., 2009; Huang et al., 2010; Simakajornboon et al., 2004; St-John and Leiter, 1999; Zhao et al., 2016), though the differences between nicotine exposed and control animals is small in some studies (e.g., (Robinson et al., 2002) and not detectable in others (Bamford and Carroll, 1999; Bamford et al., 1996). A $N_2$ challenge was used to provide a severe but brief hypoxic stimulus, and the dual chamber approach detected an increase in $\dot{v}_I$ and $\dot{v}_I/\dot{v}O_2$ in controls. In contrast, the increase in $\dot{v}_I$ in response to $N_2$ was smaller in the nicotine exposed pups, and $\dot{v}_I/\dot{v}O_2$ did not change in these animals. In conclusion, the dual chamber approach described here adds another option for the simultaneous measurement of pulmonary ventilation and metabolic rate in neonatal rodents. Moreover, the system can be constructed from inexpensive materials making it a good option for investigators that do not want to invest in a commercial plethysmography system.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A system for simultaneous measurement of pulmonary ventilation and metabolic rate, comprising:

a dual-chamber plethysmograph device including:

a body defining a dual chamber configuration, including:

a first chamber configured to receive a body of a test subject with a head of the test subject extending outside the first chamber, and a second chamber defining a size greater than the first chamber and surrounding at least a portion of the first chamber, the second chamber including gas outflow ports, a pneumotach fluidly coupled to the first chamber that generates an airflow signal indicative of pulmonary ventilation of the test subject; and a gas analyzer pump including $O_2$ and $CO_2$ sensors fluidly coupled to at least one of the gas outflow ports of the second chamber and configured to pull air through the dual-chamber plethysmograph and detect a rate of flow and concentrations of $O_2$ and $CO_2$ gas exiting the second chamber to measure a metabolic rate of the test subject.

2. The system of claim 1, further comprising a vest sized for a neonatal rodent including one or more electrodes for obtaining a measurement of EKG to obtain heart rate of the test subject, wherein lead wires from the electrodes pass through holes in at least one of the first chamber and the second chamber to an external amplifier.

3. The system of claim 1, further comprising a thermocouple probe attached to a control unit that maintains chamber temperature of the device by controlling a heat lamp.

4. The system of claim 1, wherein two ports of the pneumotach are attached to positive and negative ports of a pressure transducer.

5. The system of claim 1, wherein the gas analyzer is configured to pull air through the second chamber for open circuit measurement of metabolic rate.

6. A device for simultaneous and improved measurement of pulmonary ventilation and metabolic rate, comprising:
   a body defining a dual chamber configuration, including:
      a first chamber configured for a head-out plethysmograph, and
      a second chamber defining a size greater than the first chamber, the first chamber being disposed within the second chamber along a channel of the second chamber,
      the second chamber including
         at least one gas inflow port and at least one gas outflow port configured to permit a bias flow of gas through the second chamber,
         a gas analyzer fluidly coupled to the at least one gas outflow port of the second chamber, the gas analyzer including $O_2$ and $CO_2$ sensors that determine a metabolic rate of a test subject from gas exiting the second chamber, and
         at least one sensor associated with the first chamber and configured to generate a signal indicative of pulmonary ventilation of the test subject while the metabolic rate is determined from the gas analyzer.

7. The device of claim 6, further comprising:
   a plurality of ports defined along the second chamber to accommodate connection to tubing for gas inflow and outflow.

8. The device of claim 6, further comprising:
   a vest including one or more electrodes for obtaining a measurement of EKG to obtain heart rate of the test subject, the vest being configured to be worn by the test subject while the test subject is positioned within the first chamber.

9. The device of claim 6, wherein the body is configured to position the test subject such that a head of the test subject is positioned outside the first chamber but sealed from the environment by nature of the second chamber with exception of a predetermined bias flow of gas fed to the body.

10. The device of claim 6, wherein the body is configured for air to be pulled through the second chamber an $O_2$ and $CO_2$ analyzer for open circuit measurement of metabolic rate of the test subject.

11. The device of claim 6, wherein the body is configured to receive a Luer lock fitting in communication with tubing to interconnect the body with a pneumotachometer for pulmonary function testing.

12. The device of claim 6, further comprising one or more holes formed along the body to accommodate EKG wires and thermocouple.

13. The device of claim 6, further comprising an access slot formed into an open end of the second chamber that accommodates the first chamber to be inserted within the second chamber along the channel.

14. The device of claim 6, further comprising inflow and outflow ports defined along the body for feeding gas through the body.

15. The device of claim 6, further comprising one or more recording devices including a thermocouple probe attached to a control unit that maintains chamber temperature of the device by controlling a heat lamp.

16. A method for improved measurement of pulmonary ventilation and metabolic rate, comprising:
   positioning a test subject in a first chamber configured for a head-out plethysmograph so that a head of the test subject extends outside the first chamber;
   positioning the first chamber within a channel defined by a second chamber to define a dual chamber configuration with the second chamber surrounding at least a portion of the first chamber;
   flowing a bias gas through the second chamber between at least one gas inflow port and at least one gas outflow port of the second chamber;
   measuring a respiratory signal associated with the first chamber to obtain a pulmonary ventilation parameter of the test subject; and
   measuring $O_2$ and $CO_2$ concentrations of gas exiting the second chamber at the at least one gas outflow port with a gas analyzer and determining a metabolic rate of the test subject from the measured $O_2$ and $CO_2$ concentrations while the pulmonary ventilation parameter is measured.

17. The method of claim 16, further comprising:
   forming an access slot along an open end of the second chamber to accommodate insertion of the first chamber within the channel of the second chamber.

18. The method of claim 17, further comprising positioning a lid along the open end of the second chamber adjacent the access slot to seal the first chamber within the channel of the second chamber.

19. The method of claim 16, further comprising forming a plurality of ports along the second chamber to accommodate connection to tubing for gas inflow and outflow.

20. The method of claim 16, further comprising providing a vest including a plurality of electrodes positioned along the vest for monitoring a heart rate of the test subject positioned within the second chamber.

* * * * *